(12) United States Patent
Guo et al.

(10) Patent No.: US 10,772,885 B2
(45) Date of Patent: Sep. 15, 2020

(54) COMPOSITION FOR TREATING OCULAR DISEASES AND METHODS OF USAGE AND MAKING

(71) Applicant: REYOUNG (SUZHOU) BIOLOGY SCIENCE & TECHNOLOGY CO., LTD., Suzhou, Jiangsu (CN)

(72) Inventors: Shuhua Guo, Jiangsu (CN); Jiewen Zhong, Jiangsu (CN); Xinting Yuan, Jiangsu (CN); Zongren Yao, Jiangsu (CN)

(73) Assignee: REYOUNG (SUZHOU) BIOLOGY SCIENCE & TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 16/336,204

(22) PCT Filed: May 19, 2017

(86) PCT No.: PCT/CN2017/084994
§ 371 (c)(1),
(2) Date: Mar. 25, 2019

(87) PCT Pub. No.: WO2018/054077
PCT Pub. Date: Mar. 29, 2018

(65) Prior Publication Data
US 2019/0224194 A1  Jul. 25, 2019

(30) Foreign Application Priority Data

Sep. 26, 2016  (CN) .......................... 2016 1 0849023

(51) Int. Cl.
*A61K 31/497*  (2006.01)
*A61K 9/107*  (2006.01)
(Continued)

(52) U.S. Cl.
CPC .......... *A61K 31/497* (2013.01); *A61K 9/0048* (2013.01); *A61K 9/0051* (2013.01);
(Continued)

(58) Field of Classification Search
CPC .............. A61K 2300/00; A61K 31/355; A61K 31/496; A61K 31/497; A61K 45/06;
(Continued)

(56) References Cited

U.S. PATENT DOCUMENTS

2013/0017239 A1* 1/2013 Viladot Petit ........ A61K 9/0014
424/401

FOREIGN PATENT DOCUMENTS

CN      106902117 A    6/2017
WO   WO-2014/074823 A1   5/2014
(Continued)

OTHER PUBLICATIONS

Huu et al., "Light-responsive nanoparticle depot to control release of a small molecule angiogenesis inhibitor in the posterior segment of the eye", Journal of Controlled Release, 2015, pp. 71-77, vol. 200, 2015 Elsevier B.V.
(Continued)

*Primary Examiner* — Savitha M Rao
(74) *Attorney, Agent, or Firm* — Foley & Lardner LLP

(57) ABSTRACT

The disclosure generally relates to methods of treating an ocular disease, comprising administering an effective amount of a pharmaceutical composition to an eye of a subject in need thereof, wherein the pharmaceutical composition comprises nintedanib, or its salt, derivative, analog or polymorph, or combination thereof. The disclosure also relates to pharmaceutical composition or formulation, which can be used for treating ocular diseases. In another aspect, the disclosure provides method of making the pharmaceutical composition or formulation.

7 Claims, 4 Drawing Sheets

Nintedanib

Nintedanib ethanesulfonate (51) Int. Cl.
| | |
|---|---|
| A61K 45/06 | (2006.01) |
| A61K 31/496 | (2006.01) |
| A61P 27/02 | (2006.01) |
| A61K 9/06 | (2006.01) |
| A61K 9/127 | (2006.01) |
| A61K 9/00 | (2006.01) |
| A61K 31/355 | (2006.01) |
| A61P 27/06 | (2006.01) |
| A61P 27/12 | (2006.01) |
| A61K 47/10 | (2017.01) |
| A61K 47/14 | (2017.01) |
| A61K 9/48 | (2006.01) |
| A61K 47/32 | (2006.01) |
| A61K 47/38 | (2006.01) |
| A61K 47/44 | (2017.01) |

(52) U.S. Cl.
CPC .............. *A61K 9/06* (2013.01); *A61K 9/107* (2013.01); *A61K 9/127* (2013.01); *A61K 31/355* (2013.01); *A61K 31/496* (2013.01); *A61K 45/06* (2013.01); *A61K 47/10* (2013.01); *A61K 47/14* (2013.01); *A61P 27/02* (2018.01); *A61P 27/06* (2018.01); *A61P 27/12* (2018.01); *A61K 9/1271* (2013.01); *A61K 9/48* (2013.01); *A61K 47/32* (2013.01); *A61K 47/38* (2013.01); *A61K 47/44* (2013.01)

(58) Field of Classification Search
CPC ........ A61K 47/10; A61K 47/14; A61K 47/32; A61K 47/38; A61K 47/44; A61K 9/0048; A61K 9/0051; A61K 9/06; A61K 9/107; A61K 9/127; A61K 9/1271; A61K 9/48; A61P 27/02; A61P 27/06; A61P 27/12
See application file for complete search history.

(56) References Cited

FOREIGN PATENT DOCUMENTS

| | | |
|---|---|---|
| WO | WO-2015/041294 A1 | 3/2015 |
| WO | WO-2016/200688 A1 | 12/2016 |
| WO | WO-2016209555 A1 * | 12/2016 ............. A61K 9/146 |

OTHER PUBLICATIONS

International Search Report & Written Opinion of the International Searching Authority issued in corresponding International Application No. PCT/CN/2017/084994 dated Aug. 25, 2017.

* cited by examiner

FIG. 1

Nintedanib

Nintedanib ethanesulfonate

| | Right Eye | | Left Eye | |
|---|---|---|---|---|
| | Fundus photography | Late-phase fluorescein angiograms | Fundus photography | Late-phase fluorescein angiograms |
| Group 1 |  |  |  |  |
| Group 2 |  |  |  |  |
| Group 3 |  |  |  |  |
| Group 4 |  |  |  |  |
| Group 5 |  |  |  |  |
| Group 6 |  |  |  |  |

COMPOSITION FOR TREATING OCULAR DISEASES AND METHODS OF USAGE AND MAKING

CROSS-REFERENCE TO RELATED PATENT APPLICATIONS

This application is a 371 of PCT/CN2017/084994, filed May 19, 2017, which claims priority under 35 U.S.C. § 119(d) to Chinese Application No. CN App. No. 2016108490239 filed Sep. 26, 2016. Contents of the above applications are incorporated herein by reference.

FIELD

The present disclosure relates to composition for treating ocular diseases (e.g., age-related macular degeneration) and methods of usage and making.

BACKGROUND

Age-related macular degeneration ("AMD"), a progressive retinal disease, is the leading cause of blindness, particularly among patients over 65 years old. In the U.S., approximately 15 million patients are affected by AMD, and the prevalence of this disease among elder patients increases exponentially in the last decade. Patients with AMD experience gradual worsening of vision and eventually develop blurred or no vision in the central area of the visual field (or the macular). Exudative neovascular (wet form) and non-neovascular (dry form) are two major kinds of AMD. While macula thinning and pigmentation disturbance are observed in dry form, wet form is often associated with abnormal blood vessels growing under retina and macula. Vision deterioration caused by wet form progresses more rapidly than dry form. Wet form, characterized by choroidal neovascularization (CNV), leads to 80% to 90% of severe vision loss associated with AMD.

Vascular endothelial growth factor (VEGF) inhibitors are commonly used for treating AMD and a wide variety of other retinal diseases, e.g., diabetic retinopathy, retinal vein occlusions (RVOs), neovascular glaucoma, retinopathy of prematurity (ROP), and intraocular tumors. Intravitreal injection of VEGF inhibitors (bevacizumab, pegaptanib, ranibizumab, or aflibercept) has shown its efficacy in treating wet AMD.

However, intravitreal injection of VEGF inhibitors poses the risk of post-injection- and drug-class-associated adverse events. The incidence of infectious endophthalmitis per patient was reported in ranges from 0.019 to 1.6%. See Scott et al., *Retina*, 27: 10-12 (2007). Intravitreal injection of VEGF inhibitors is also associated with intraocular inflammation, rhegmatogenous retinal detachment, intraocular pressure elevation, and ocular hemorrhage. Falavarjani et al., *Eye*, 27, 787-794 (2013). The monthly injections and clinical assessment necessitated by anti-VEGF therapy impose additional drain on patients and clinicians required to follow a stringent, tedious treatment regime.

For CNV, there has not been an effective, proven therapy. Though laser photocoagulation may be used in limited population to remove CNV, the procedure can also affect the viable photoreceptors overlying the visual area affected by CNV, resulting in immediate visual acuity loss. Photodynamic therapy may avoid the side effect on the overlying visual area, but patients treated by photodynamic therapy often experience elevated intra-ocular pressure and sensitivity to light for days.

These highlight a need for a more effective, easily administration method or pharmaceutical composition for treating ocular diseases (e.g., AMD and CNV) or for delaying or reversing onset of the vision loss and/or blurring caused by the ocular diseases.

SUMMARY OF THE INVENTION

Figure 1:
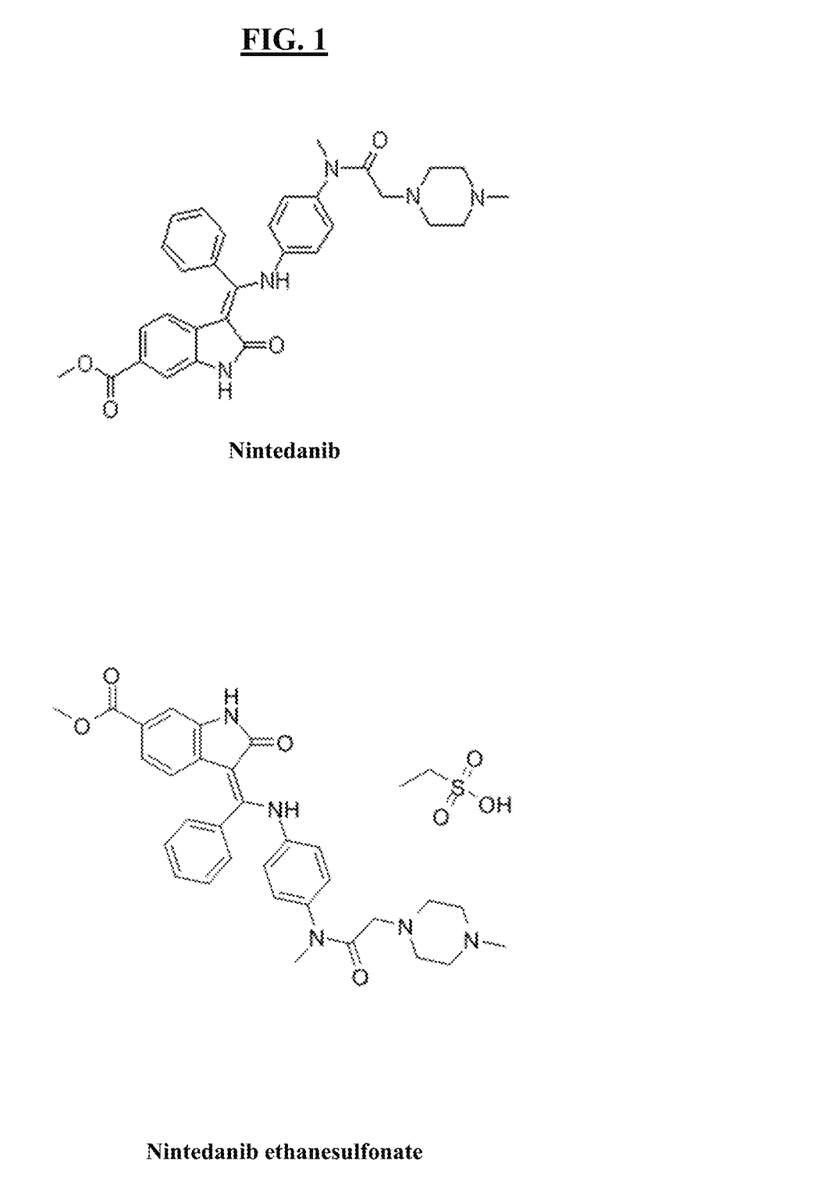
FIG. 1 shows chemical structures of nintedanib and nintedanib ethanesulfonate.

Nintedanib (IUPAC name: methyl (3Z)-3-[[4-[methyl-[2-(4-methylpiperazin-1-yl)acetyl]amino]anilino]-phenylmethylidene]-2-oxo-1H-indole-6-carboxylate) is a recently discovered angiogenesis inhibitor that can simultaneously act on three key receptor families involved in angiogenesis: vascular endothelial growth factor receptor (VEGFR), platelet-derived growth factor receptor (PDGFR) and fibroblast growth factor receptor (FGFR). The structure of Nintedanib is shown in FIG. 1. Nintedanib has been approved by FDA and EMA to treat idiopathic pulmonary fibrosis (IPF), and was also approved by EMA in combination with docetaxel to be used for adenocarcinoma, locally advanced or metastatic or locally recurrent non-small cell lung cancer (NSCLC) in adult patients diagnosed with histological methods after first-line chemotherapy.

This disclosure provides methods of treating an ocular disease, comprising administering an effective amount of a pharmaceutical composition to an eye of a subject in need thereof, wherein the pharmaceutical composition comprises nintedanib, or its salt, derivative, analog or polymorph, or combination thereof.

In one aspect, the disclosure also relates to pharmaceutical compositions for treating an ocular disease, comprising nintedanib, or its salt, derivative, analog, polymorph, or combination thereof. In some embodiments, the disclosure provides a pharmaceutical eye drop formulation which comprises 5 to 20 mg/mL nintedanib ethanesulfonate, 50 to 200 mg/mL medium chain triglyceride, 5 to 30 mg/mL soybean lecithin, 2 to 20 mg/mL cholesterol, 0.05 to 0.5 mg/mL benzalkonium chloride, and 0.1 to 1 mg/mL vitamin E. In another embodiment, the formulation comprises Tween 80 and/or polyoxyethylene castor oil.

In another aspect, the disclosure provides methods of preparing a pharmaceutical formulation suitable for administering to a subject in need thereof, comprising: (a) micronizing a composition comprising nintedanib, or its salt, derivative, analog or polymorph, or combination thereof; and (b) mixing the micronized composition with other ingredients. In another embodiment, the method further comprises sonicating the mixture to form an emulsion.

DETAILED DESCRIPTION

After reading this description, it will become apparent to one skilled in the art how to implement the invention in various alternative embodiments and alternative applications. However, not all embodiments of the present invention are described. It will be understood that the embodiments presented here are presented by way of an example only, and not limitation. This detailed description of various alternative embodiments should not be construed to limit the scope or breadth of the present invention.

Before the present invention is disclosed and described, it is to be understood that the aspects described below are not limited to specific compositions, methods of preparing such compositions, or uses thereof may vary. It is also to be understood that the terminology used is to describe particular aspects only and is not intended to be limiting.

Definitions

Unless defined otherwise, all technical and scientific terms used have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to limit the invention. As used herein, the singular forms "a," "an" and "the" are intended to include the plural forms as well, unless the context clearly indicates otherwise.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "comprising" or "comprises" is intended to mean that the compositions and methods include the recited elements, but do not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The term "ocular disease," as used here, refers to any eye diseases. Non-limiting examples of ocular diseases include age-related macular degeneration ("AMD"), choroidal neovascularization ("CNV"), retinal detachment, diabetic retinopathy, atrophy of retinal pigment epithelium, hypertrophy of retinal pigment epithelium, retinal vein occlusion, choroidal retinal vein occlusion, macular edema, anterior angiogenesis, cornea angiogenesis, pterygium conjunctiva, subretinal edema, choroidal neovascularization, cystoid macular edema, epiretinal membrane, macular hole, vascular streaks, pigmented retinitis, Stuttgart disease, glaucoma, cataract, inflammatory condition, refractory abnormalities, conical cornea, retinopathy of prematurity, retinal edema, and high myopia. In one embodiment, the ocular disease is AMD. In another embodiment, the ocular disease is CNV.

The term "age-related macular degeneration" or "AMD," as used herein, denotes a retinal disease that is known in the art. In some embodiments, AMD is any stages of the retinal disease, including but not limited to, Category 2 (early stage), Category 3 (intermediate) and Category 4 (advanced) AMD.

In one embodiment, AMD is generally classified as two types: dry form and wet form. The term "dry form" refers to one type of AMD, in which the deterioration of the retina is associated with the formation of small yellow deposits (drusen) under the macula. In some embodiments, the dry from AMD is often associated with choroidal capillary atrophy, fibrosis, Bruch's membrane thickening, and macular atrophy degeneration caused by retinal pigment epithelial atrophy.

The term "wet form" denotes an AMD with abnormal blood vessels developed under the retina towards the macula. The abnormal blood vessels, when breaking and bleeding, can damage the macula and cause its dislocation from its base. The symptoms of wet form AMDs include but are not limited to the destruction of the Bruch's membrane, glass membrane, choroidal vascular invasion of subretinal to form choroidal neovascularization (CNV), and then the macular retinal pigment subepithelial or neural subepithelial causes serous or hemorrhagic disciform detachment and ultimately becomes disciform scar. According to the clinical observation, atrophy type can also change into exudative type.

In some embodiments, the wet AMD is also called choroidal neovascularization ("CNV"). CNV (or wet form) can be further classified into "classic" CNV and "occult" CNV. Classic CNV is generally characterized by a well-demarcated area of bright hyperfluorescence throughout the transit phase of the angiogram with leakage in the mid and late phase frames. Occult CNV includes fibrovascular pigment epithelial detachment. The newly formed vessels caused by CNV have a tendency to leak blood and fluid, causing symptoms of scotoma and metamorphopsia. The new vessels are accompanied by proliferation of fibrous tissue. This complex of new vessels and fibrous tissue can destroy photoreceptors. The lesion can continue to grow throughout the macula, resulting in progressive, severe, and irreversible vision loss. Once one eye of an individual develops CNV, the fellow eye has about a 50% chance of developing a similar CNV lesion within 5 years.

In some embodiments, the CNV lesion of the disclosure comprises occult CNV. In one embodiment, the CNV lesion comprises, alternatively consists essentially of, or yet consists of classic CNV. In another embodiment, the CNV lesion comprises both classic CNV and occult CNV.

The term "solvate," as used here, refers to a compound with which solvent molecules form a stoichiometric solid complex. Non-limiting examples of solvent molecules include ethanol, methanol, or salts.

The term "hydrate" refers to a specific form of solvate, where the solvent molecule is water. In one embodiment, the hydrate of the compound of the present invention or a salt thereof is a stoichiometric composition of the compound or salt with water, such as hemihydrate, monohydrate, or dihydrate.

The term "salt" means a pharmaceutically acceptable salt of the compound in this invention. In one embodiment, suitable pharmaceutically acceptable salts are salts of inorganic or organic acids. Non-limiting examples of organic acids include, but are not limited to hydrochloric acid, sulfuric acid, phosphoric acid, hydrobromic acid, methanesulfonic acid, trifluoromethanesulfonic acid, benzenesulfonic acid, p-toluenesulfonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid and mandelic acid. In another embodiment, pharmaceutically acceptable salts include salts of inorganic bases such as salts containing alkali cations (e.g., Li+, Na+ or K+), alkaline earth cations (e.g., Mg2+, Ca2+ or Ba2+), ammonium cations; and acid salts of organic bases (e.g., aliphatic and aromatic substituted ammonium and quaternary ammonium cations such as those derived from triethylamine, N,N-diethylamine, N,N-dicyclohexylamine, lysine, pyridine, N,N-dimethylaminopyridine (DMAP)), 1,4-diazabicyclo [2.2.2] octane (DABCO), 1,5-diazabicyclo [4,3,0] non-5-ene (DBN), 1,8-diazabicyclo [5.4.0] undec-7-ene (DBU), and their protonated or fully alkylated salts.

The term "therapeutic agent," as used herein, denotes an agent or a compound that provides a desired biological or pharmacological effect when administered to a subject (e.g., human or animal). For example, the AMD therapeutic agent provides desired biological or pharmacological effect when administered to a subject affected by AMD. In one embodiment, the AMD therapeutic agent comprises, alternatively consists essentially of, or yet consists of a VEGF inhibitor, a PDGF inhibitor, or an FGF inhibitor.

In another embodiment, the AMD therapeutic agent comprises, alternatively consists essentially of, or yet consists of E10030, sirolimus, infliximab, POT-4, JSM6427, volociximab, ALG-1001, ATG003, AdPEDF. 11, methotrexate, triple combination therapy (verteporfin-ranibizumab-dexamethasone). In one embodiment, the pharmaceutical composition is administered intraocularly, intravitreally, intravenously, subcutaneously, orally, or intraperitoneally. In another embodiment, the pharmaceutical composition is in a form of an eye drop, an oculentum, a collyrium, an ointment, a lysosome, a gel, a liquid, a liposome, a microcapsule, a microsphere, or an intraocular injection.

The terms "sustained release," "slow-release," "controlled release," "modified release," and "extended release," used interchangeably, denote a release of an active ingredient that occurs more slowly relative to an immediate release dosage form. In one embodiment, the sustained release property of a composition is measured and confirmed by an in vitro dissolution method and an in vivo blood concentration-time profile.

In one embodiment, the sustained release composition has an in vitro dissolution rate of no more than about 10%, 20%, 30%, 40%, 50%, 60%, 70%, 80%, or 90% of the active ingredient released after 2 hours, no more than about 20%, 30%, 40%, 50%, 60%, 70%, 80%, or 90% of the active ingredient released after 4 hours, no more than about 30%, 40%, 50%, 60%, 70%, 80%, or 90% of the active ingredient released after 6 hours, no more than about 40%, 50%, 60%, 70%, 80%, or 90% of the active ingredient released after 8 hours, no more than about 50%, 60%, 70%, 80%, or 90% of the active ingredient released after 10 hours, no more than about 60%, 70%, 80%, or 90% of the active ingredient released after 12 hours, and/or no more than about 70%, 80%, or 90% of the active ingredient released after 16 hours.

The term "micronize," "micronized," and "micronization," used interchangeable in this disclosure, denotes reduction of the average size of a material's particles. In one embodiment, micronization is used when the particles that are produced are only a few micrometers (µm) or less than 1 µm in diameter. Micronization can be achieved by processes including, but not limited to, jet milling, pearl-ball milling, high-pressure homogenization, the RESS process (Rapid Expansion of Supercritical Solutions), the SAS method (Supercritical Anti-Solvent), or the PGSS method (Particles from Gas Saturated Solutions).

In one embodiment, the average particle size of the micronized material is between about 5 µm and about 200 µm. In another embodiment, the average particle size is at least about 5 µm. In another embodiment, the average particle size is at least about 10 µm. In another embodiment, the average particle size of the base granular starch is between about 5 µm and about 20 µm. In another embodiment, the average particle size of the base granular starch is between about 5 µm and about 100 µm. In another embodiment, the mean average particle size of the micronized composition is between about 2 µm and about 4 µm. In another embodiment, the average particle size is less than about 3 µm. In another embodiment, the average particle size is less than about 2 µm. In another embodiment, the average particle size is less than about 1 µm.

The term "sustained release intraocular implant" refers to a slow-release composition or ingredient that is implanted to an ocular area.

The term "matrix," as used herein, refers to a material intended to interface with biological systems to treat, augment, or replace any tissue or function of the tissue depending on the material either permanently or temporarily. The matrix can serve as a delivery device for nintedanib (or its salt, derivative, analog, solvate, hydrate, or polymorph) incorporated therein and/or as a cell-ingrowth matrix.

The matrices described herein are formed from liquid precursor components which are able to form a scaffold outside or inside the body at the site of need. In some embodiments, the matrix is in the form of a liquid, semi-solid, such as a paste, or a solid. Depending on the type of precursor materials, the matrix may be swollen with water but not dissolved in water, i.e., form a hydrogel which stays in the body for a certain period of time.

The terms "patient," "subject," "individual," and the like are used interchangeably herein and refer to any animal, or cells thereof, whether in vitro or in situ, amenable to the methods described herein. In a preferred embodiment, the patient, subject, or individual is a mammal. In some embodiments, the mammal is a mouse, a rat, a guinea pig, a non-human primate, a dog, a cat, or a domesticated animal (e.g., horse, cow, pig, goat, sheep). In a preferred embodiment, the patient, subject, or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. For example, treatment of an ocular disease includes, but is not limited to, elimination of lowing or preventing the onset of the ocular disease, reducing the risk of the ocular disease, or arresting the development of the ocular disease.

The term "nintedanib" refers to a nintedanib compound, a nintedanib derivative, a nintedanib analog, a nintedanib salt, a nintedanib solvate, a nintedanib hydrate a nintedanib polymorph, or a portion thereof, which has or is capable of promoting at least one of the biological responses normally associated with nintedanib. In one embodiment, nintedanib is nintedanib ethanesulfonate. Non-limiting examples of nintedanib polymorphs are disclosed in WO2016178064 and U.S. Pat. No. 7,119,093, each of which is incorporated by reference in its entirety.

The term "administering" or "administration" of an agent to a subject includes any route of introducing or delivering to a subject a compound to perform its intended function. Administration can be carried out by any suitable route, including intraocularly, intravitreally, orally, intranasally, parenterally (intravenously, intramuscularly, intraperitoneally, or subcutaneously), or topically. Administration includes self-administration and the administration by another.

The term "analog" refers to a compound in which one or more individual atoms or functional groups have been replaced, either with a different atom or a different functional group, generally giving rise to a compound with similar properties. In some aspect, the analog refers to a structure that is similar to another but differs in one or two components.

The term "derivative" refers to a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "pharmaceutically acceptable carrier" denotes a carrier that is conventionally used in the art to facilitate the storage, administration, and/or healing effect of a biologically active agent. Non-limiting examples of pharmaceutically acceptable carriers include oleoylpolyethylene glycol glyceride, linoleoylglycol glycol glyceride, lauroyl polyglycol glyceride, liquid paraffin, light liquid paraffin, soft paraffin (petrolatum), hard paraffin, wax, castor oil, peanut oil, sesame oil, medium chain triglycerides, cetearyl alcohol, lanolin, glycerol, propylene glycol, polyethylene glycol (PEG), or water.

The term "excipient" as used herein refers to a non-therapeutic agent added to a pharmaceutical composition to provide a desired consistency or stabilizing effect. Non-limiting examples of excipients include a surfactant, a gelling agent, an organic co-solvent preservative, a fungicide or an antibacterial agent, a pH adjuster, an isotonic agent, a chelating agent, a buffer, a stabilizer, an antioxidant, a thickener, or a combination thereof.

The term "surfactant," as used herein, denotes a molecule that comprises both hydrophobic and hydrophilic portions, which allows it to stabilize and disperse hydrophobic molecules and aggregates of hydrophobic molecules in aqueous systems.

The term "gelling agent" refers to a substance that promotes the property of a composition to form a gel. As used herein, the term "gel" refers to a more or less firm cohesive internal structure behaving like a solid. In one embodiment, the gel does not flow or does not substantially flow in its steady-state.

The term "preservative" or "preservative agent" refers to an agent in the ophthalmic compositions for the purpose of inhibiting the growth of microorganisms in the product, thereby helping to maintain sterility of the composition.

The term "emulsion" is referring hereinafter to any mixture comprising water and organic agent (e.g., oil). In some embodiments, the emulsions are in the form of aggregates, vesicles, micelles, reversed micelles, nano-emulsions, micro-emulsion, liposomes or in any combination thereof. The term "emulsifier" refers to any material or molecule provided as a polymer, oligomer or monomer and is non-ionic, anionic or cationic detergent and/or surfactant. In one embodiment, the emulsifier comprises both lipophilic and hydrophilic portions, such as in saturated or non-saturated long chain alkyl comprising at least one polar or charged atom.

The term "water" refers to water or water solutions. In some embodiments, the water is any natural or purified, distilled, filtered, de-ionized water, water suspension, water-miscible solvent or diluent, water miscible aqueous phase or water-miscible emulsion or any combination thereof.

The term "capsule" refers to any delivery system of a substance. In some embodiments, a capsule contains an active ingredient to be delivered to eyes. In one embodiment, a capsule contains nintedanib, or its salt, derivative, analog, solvate, hydrate, or polymorph, or combination thereof.

The term "isotonic agent" refers to a component that functions to partially maintain isotonicity of a formulation and/or at least partially maintain the level, ratio, or proportion of the therapeutically active ingredient present in the formulation.

The term "pH adjuster," as used herein, refers to an acid, a base, or a pH buffer. The pH adjuster is used to adjust the pH in a solution so that the solution pH falls within or increases above a selected pH value.

The term "chelating agent," as used herein, relates to polyfunctional compounds having a chelating group and at least one pendant linker group, wherein the chelating group is capable of chelating with another molecule, and the pendant linker group is capable of covalently binding to one or more targeting molecules.

The term "w/v" as used herein refers to weight/volume. For example, for a solution comprising a certain compound in a concentration of 1% w/v, 1 L of that solution comprises 10 g of that compound.

The term "therapeutically effective amount" or "effective amount" refers to an amount of the agent that, when administered, is sufficient to cause the desired effect. For example, an effective amount of a composition may be an amount sufficient to treat, control, alleviate, or improve the symptoms or conditions related to ocular diseases. The therapeutically effective amount of the agent may vary depending on the pathogen being treated and its severity as well as the age, weight of the patient to be treated. The skilled artisan will be able to determine appropriate dosages depending on these and other factors. The compositions can also be administered in combination with one or more additional therapeutic agents or compounds. In the methods described herein, the therapeutic compounds may be administered to a subject having one or more signs or symptoms of a disease or disorder.

Nintedanib (IUPAC name: methyl (3Z)-3-[[4-[methyl-[2-(4-methylpiperazin-1-yl)acetyl]amino]anilino]-phenylmethylidene]-2-oxo-1H-indole-6-carboxylate) is a recently discovered angiogenesis inhibitor that can simultaneously act on three key receptor families involved in angiogenesis: vascular endothelial growth factor receptor (VEGFR), platelet-derived growth factor receptor (PDGFR) and fibroblast growth factor receptor (FGFR). The structure of nintedanib is shown in FIG. 1.

Nintedanib has been approved by the FDA and EMA for the treatment of idiopathic pulmonary fibrosis (IPF), also approved by the EMA in combination with docetaxel to be used for adenocarcinoma, locally advanced or metastatic or locally recurrent non-small cell lung cancer (NSCLC) in adult patients diagnosed with histological methods after first-line chemotherapy.

Age-related macular degeneration (AMD), mostly incurred after age 45 with the prevalence increased with age, is one of the important diseases that causes blindness in the elderly currently. The disease is divided into two types: dry (also called non-exudative) and wet (also called exudative). The dry type is mainly choroidal capillary atrophy, fibrosis, Bruch's membrane thickening, and macular atrophy degeneration caused by retinal pigment epithelial atrophy; the wet type is mainly the destruction of the Bruch's membrane, glass membrane, choroidal vascular invasion of subretinal to form choroidal neovascularization (CNV), and then the macular retinal pigment subepithelial or neural subepithelial causes serous or hemorrhagic disciform detachment and ultimately becomes disciform scar. According to the clinical observation, atrophy type can also change into exudative type.

Vascular Endothelial Growth Factor Receptor (VEGF) pathway is a classic angiogenic signaling pathway that can be used to treat multiple solid tumors and wet age-related macular degeneration (AMD). Monoclonal antibodies or fusion proteins which have been approved by the FDA targeting VEGF include: Avastin, Lucentis, Eylea, Cyramza, and Conbercept (also known as "Lumitin") that was developed by a Chinese company and launched in 2013. However, no small molecule drugs targeting VEGF, PDGF, and FGF for the treatment of ocular conditions have been launched.

This highlights an urgent need to design more effective methods for treating ocular diseases such as AMD and to discover pharmaceutical compositions with improved therapeutic effects against ocular diseases.

In view of the foregoing, it is an object of the present invention to provide the use of nintedanib (or its salt, derivative, analog, solvate, hydrate, or polymorph) as an ophthalmic pharmaceutical composition. The composition has sufficient stability and is effective against ocular diseases, when applied in the eye, in particular the rear of the eye (for example, in the retina, Bruch membrane, and choroidal region).

In one embodiment, the ocular diseases comprise age-related macular degeneration ("AMD"), choroidal neovascularization ("CNV"), retinal detachment, diabetic retinopathy, atrophy of retinal pigment epithelium, hypertrophy of retinal pigment epithelium, retinal vein occlusion, choroidal retinal vein occlusion, macular edema, anterior angiogenesis, cornea angiogenesis, pterygium conjunctiva, sub-retinal edema, choroidal neovascularization, cystoid macular edema, epiretinal membrane, macular hole, vascular streaks, pigmented retinitis, Stuttgart disease, glaucoma, cataract, inflammatory condition, refractory abnormalities, conical cornea, retinopathy of prematurity, retinal edema, or high myopia.

Methods of Treating Ocular Diseases

Age-related macular degeneration (AMD) causes severe, irreversible vision loss and is the leading cause of blindness in elders. There are two major categories of AMD—dry form and wet form. Patients with dry form are often characterized by drusen and atrophic changes in the retinal pigment epithelium (RPE). The wet form, also known as choroidal neovascularization (CNV), causes a majority of severe vision loss due to AMD. CNV is caused by ingrowth of choroidal capillaries through a break in the outer aspects of Bruch's membrane. Each year, more than 70,000 individuals over the age of 65 develop CNV in the US. CNV (or wet form) can be further classified into "classic" CNV and "occult" CNV. Classic CNV is generally characterized by a well-demarcated area of bright hyperfluorescence throughout the transit phase of the angiogram with leakage in the mid and late phase frames. Occult CNV includes fibrovascular pigment epithelial detachment. The newly formed vessels caused by CNV have a tendency to leak blood and fluid, causing symptoms of scotoma and metamorphopsia. The new vessels are accompanied by proliferation of fibrous tissue. This complex of new vessels and fibrous tissue can destroy photoreceptors. The lesion can continue to grow throughout the macula, resulting in progressive, severe, and irreversible vision loss. Once one eye of an individual develops CNV, the fellow eye has about a 50% chance of developing a similar CNV lesion within 5 years.

In some embodiments, the CNV lesion of the disclosure comprises occult CNV. In one embodiment, the CNV lesion comprises, alternatively consists essentially of, or yet consists of classic CNV. In another embodiment, the CNV lesion comprises both classic CNV and occult CNV. A lesion in which the area of classic CNV occupies more than 0%, but less than 50% is termed "minimally classic". A lesion in which the area of classic CNV occupies at least 50% of the area of the entire lesion is termed "predominantly classic."

Thus, this disclosure provides a method of treating an ocular disease, comprising, alternatively consisting essentially of, or yet consisting of administering an effective amount of a pharmaceutical composition to an eye of a subject in need thereof, wherein the pharmaceutical composition comprises nintedanib, or its salt, derivative, analog, solvate, hydrate, or polymorph, or combination thereof. In one embodiment, the pharmaceutical composition comprises, alternatively consists essentially of, or yet consists of 0.01 mg/mL to 20 mg/mL, 0.1 mg/mL to 5 mg/mL, 0.5 mg/mL to about 4 mg/mL, 1 mg/mL to 4 mg/mL, 2 mg/mL to 3 mg/mL nintedanib, or its salt, derivative, analog or polymorph, or combination thereof. In one embodiment, the pharmaceutical composition comprises about 1 mg/mL to about 4 mg/mL comprises nintedanib, or its salt, derivative, analog or polymorph, or combination thereof. In another embodiment, the pharmaceutical composition comprises about 1 mg/mL to about 3 mg/mL nintedanib, or its salt, derivative, analog or polymorph, or combination thereof. In another embodiment, the pharmaceutical composition comprises, at least 0.01 mg/mL, 0.1 mg/mL, 0.5 mg/mL, 1 mg/mL, 5 mg/mL, 10 mg/mL, 15 mg/mL, 25 mg/mL, 50 mg/mL, or 100 mg/mL nintedanib, or its salt, derivative, analog or polymorph, or combination thereof. In some embodiments, the nintedanib salt is nintedanib ethanesulfonate.

In another aspect, the concentration of nintedanib (or its salt, derivative, analog or polymorph) in the pharmaceutical composition is at least 0.001% w/v, 0.01% w/v, 0.1% w/v, 1% w/v, 5% w/v, or 10% w/v, 15% w/v, 20% w/v, 30% w/v, 40% w/v, or 50% w/v. In another embodiment, the concentration is from 0.001% w/v to 50% w/v, 0.001% w/v to 30% w/v, from 0.01% w/v to 20% w/v, 0.01% w/v to 10% w/v, from 0.1% w/v to 10% w/v, or from 1% w/v to 5% w/v. In some embodiments, the nintedanib salt is nintedanib ethanesulfonate.

The total amount of the pharmaceutical composition applied to the eye of the eye drop described in the present invention is usually the close administered each time, administered in dosages of 0.01 to 50 mg, preferably 0.02 to 10 mg, more preferably 0.05 to 5 mg per eye, once daily or more than once, preferably up to 5 times, most preferably up to 3 times.

The chemical stability of the ophthalmic solution of the present invention is greater than 1 day, 7 days, 1 month, 2 months, 4 months, 8 months, 16 months, or 24 months. In some embodiments, the chemical stability means that the active ingredient does not degrade significantly during storage.

In some embodiments, the pharmaceutical composition is administered to any areas of eyes of the subject. In one embodiment, the pharmaceutical composition is applied to the central area of the eyes. In one embodiment, the pharmaceutical composition is applied to the macula.

In another aspect, the pharmaceutical composition comprises 0.01 mg/mL to 20 mg/mL, 0.1 mg/mL to 5 mg/mL, 0.5 mg/mL to about 4 mg/mL, 1 mg/mL to 4 mg/mL, 2 mg/mL to 3 mg/mL nintedanib ethanesulfonate. In another embodiment, the pharmaceutical composition comprises, at least 0.01 mg/mL, 0.1 mg/mL, 0.5 mg/mL, 1 mg/mL, 5 mg/mL, 10 mg/mL, 15 mg/mL, 25 mg/mL, 50 mg/mL, or 100 mg/mL nintedanib ethanesulfonate. In one embodiment, the pharmaceutical composition comprises about 1 mg/mL nintedanib ethanesulfonate. In another embodiment, the pharmaceutical composition comprises about 5 mg/mL nintedanib ethanesulfonate.

In another embodiment, the pharmaceutical composition further comprises an AMD therapeutic agent. In one embodiment, the AMD therapeutic agent comprises a VEGF inhibitor, a PDGF inhibitor, or an FGF inhibitor. In some embodiments, the AMD therapeutic agent comprises, alternatively consists essentially of, or yet consists of E10030, sirolimus, infliximab, POT-4, JSM6427, volociximab, ALG-1001, ATG003, AdPEDF.11, methotrexate, triple combination therapy (verteporfin-ranibizumab-dexamethasone). In one embodiment, the pharmaceutical composition is administered intraocularly, intravitreally, intravenously, subcutaneously, orally, or intraperitoneally. In another embodiment, the pharmaceutical composition is in a form of an eye drop, an oculentum, a collyrium, an ointment, a lysosome, a gel, a liquid, a liposome, a microcapsule, a microsphere, or an intraocular injection.

In some embodiments, the pharmaceutical composition further comprises an angiogenesis inhibitor. Non-limiting angiogenesis inhibitors include squalamine, squalamine lactate (Evizon™, Genaear Corp.), and curcumin; Vascular endothelial growth factor (VEGF) inhibitors including pegaptanib (Macugen®, Eyetech/Pfizer), bevacizumab (Avastin®, Genentech, Inc.), concentrated shark cartilage extract (Neovastat®, Eterna Zentaris), PTK 787 (vatalanib, Schering AG/Novartis), ribozyme anti-angiogenic (Angiozyme®, Sirma Therapeutics, Inc./Chiron Corp.); AZD 6474 (Zactima®, AstraZeneca AB Ltd.), anti-angiogenesis chimeric monoclonal antibody specific VEGF receptor 2 (IMC-1C11, ImClone Sys. Inc.), isocoumarin 2-(8-hydroxy-6-methoxy-1-oxo-1H-2-benzopyran-3-yl) propionic acid (NM-3, Ilex Oncology Inc.), SU668 (Pfizer), isopropoxymethyl-12-(3-hydroxypropyl) ideno[2,1-a]pyrro[3,4-c]carbazol e-5-one (CEP-5214, Cephalon), CEP-7055 (the N,N-dimethyl glycine ester prodrug of CEP-5214, Cephalon), and PTC299 (PTC Therapeutics); Integrin antagonists such as anti-αvβ3 antibody (Vitaxin®, Medimmune Inc.); RDG peptide mimetics such as S137 and S247 (Pfizer), conformationally constrained bicyclic lactam Arg-Gly-Asp-containing pseudopeptides such as ST1646 (Sigma Tau S.p.A.); DPC A803350 (Bristol-Myers Squibb), and o-guanidines (3D Pharmaceuticals Inc.); matrix metalloproteinase inhibitors such as prinomastat (AG 3340, Pfizer), (ISV-616, InSite Vision), (TIMP-3, NIH); S3304 (Shionogi); BMS 275291 (Celltech/Bristol-Myers Squibb); SC 77964 (Pfizer); ranibizumab (Lucentis®, Genentech, Inc.); ABT 518 (Abbott Labs.); CV 247 (Ivy Medical); NX-278-L anti-VEGF aptamer (EyeTech Pharm.); 2'-O-mrthoxyethyl antisense C-raf oncogene inhibitor (ISIS-13650, Isis Pharm., Inc./iCo Therapeutics, Inc.); vitronectin and osteopontin antagonists (3D Pharm.); combretastatin A-4 phosphate (CA4P, Oxi-Gene, Inc.); fab fragment α-V/β-1 integrin antagonist (Eos-200-F, Protein Design Labs); α-v/β-3 integrin antagonist (Abbott Labs.); urokinase plasminogen activator fragment (A6, Angstrom Pharm.); VEGF antagonists (including AAV-PEDF, Chiron Corp.; VEGF-R, Johnson & Johnson/Celltech; SU10944, Sugen/Pfizer; VEGF-TRAP, Regeneron; SP-(V5.2)C, Supratek Pharm. Inc.; endostatin VEGF antagonist, EntreMed, Inc. (Rockville, Md.); kdr tyrosine kinase inhibitor (EG-3306, Ark Therapeutics); cytochalasin E (NIH); kallikrein-binding protein (Medical Univ., SC); combretastatin analog (MV-5-40, Tulane); pigment-epithelium derived growth factor (Med. Univ. SC); AdPEDF, GenVec, Inc.); plasminogen kringle (Medical Univ. SC); rapamycin; cytokine synthesis inhibitor/p38 mitogen-activated protein kinase inhibitor (SB-220025, GlaxoSmithKline); FGF1 receptor antagonist/tyrosine kinase inhibitor (Pfizer/Sugen); bradykinin B1 receptor antagonist (B-9858, Cortech, Inc.); bactericidal/permeability-increasing protein (Neuprex®, Xoma Ltd.); protein kinase C inhibitor (Hypericin, Sigma-Aldrich, St. Louis, Mo.); ruboxistaurin mesylate (LY-333531, Eli Lilly & Co.); polysulphonic acid derivatives (Fuji Photo Film); growth factor antagonists such as TBC-2653 and TBC-3685 (Texas Biotech. Corp.); Tunica internal endothelial cell kinase (Amgen Inc.)

In one aspect, the effective amount per treatment for each eye is 0.01 μg to 50 μg, 0.1 μg to 25 μg, 0.5 μg to 25 μg, 1 μg to 25 μg, 2.5 μg to 10 μg, or 2.5 μg to 5 μg of nintedanib, or its salt, derivative, analog, polymorph, or combination thereof. In one embodiment, the effective amount per treatment for each eye is 0.1 μg to 25 μg of nintedanib, or its salt, derivative, analog, polymorph, or combination thereof.

In some embodiments, the effective amount per treatment for each eye is 0.5 μg to 25 μg of nintedanib, or its salt, derivative, analog, polymorph, or combination thereof. In another embodiment, the effective amount per treatment for each eye is 2.5 μg to 10 μg of nintedanib, or its salt, derivative, analog, polymorph, or combination thereof. In a different embodiment, the effective amount per treatment for each eye is 2.5 μg to 5 μg of nintedanib, or its salt, derivative, analog, polymorph, or combination thereof.

In another aspect, the ocular disease is age-related macular degeneration ("AMD"), choroidal neovascularization ("CNV"), retinal detachment, diabetic retinopathy, atrophy of retinal pigment epithelium, hypertrophy of retinal pigment epithelium, retinal vein occlusion, choroidal retinal vein occlusion, macular edema, anterior angiogenesis, cornea angiogenesis, pterygium conjunctiva, sub-retinal edema, choroidal neovascularization, cystoid macular edema, epiretinal membrane, macular hole, vascular streaks, pigmented retinitis, Stuttgart disease, glaucoma, cataract, inflammatory condition, refractory abnormalities, conical cornea, retinopathy of prematurity, retinal edema, or high myopia. In some embodiments, the ocular disease is AMD. In one embodiment, the ocular disease is CNV.

In another embodiment, the pharmaceutical composition further comprises a binding agent, a flavor agent, a lubricating agent, a flow agent, a disintegration agent, a delay agent, or combination thereof. In one embodiment, the binding agent comprises one or more of starch, modified starch, cellulose, modified cellulose, brewer's yeast, sucrose, dextrose, whey, dicalcium phosphate, or a combination thereof. In another embodiment, the flavoring agent comprises one or more of dried liver, liver extract, cheese, cheese products, natural flavors, artificial flavors, milk flavored products, soybean flavored products, brewer's yeast, or the combinations thereof. In a further embodiment, the lubricating agent comprises one or more of magnesium stearate, stearic acid, starch, modified starch, modified cellulose, or a combination thereof. In a yet another embodiment, the flow agent comprises one or more of silica dioxide, modified silica, fumed silica, talc, a combination thereof. In a different embodiment, the disintegration agent comprises one or more of croscarmellose sodium, sodium starch glycolate, starch, modified starch, or a combination thereof. In some embodiments, the delay agent comprises one or more of stearic acid, stearic acid salts, magnesium stearate, polyethylene glycols, starch, modified starch, methacrylate polymers, or a combination thereof.

In one embodiment, the pharmaceutical composition further comprises a pharmaceutically acceptable carrier or excipient. In one embodiment, the excipient comprises a surfactant, a gelling agent, an organic co-solvent preservative, a fungicide or an antibacterial agent, a pH adjuster, an isotonic agent, a chelating agent, a buffer, a stabilizer, an antioxidant, a thickener, or combination thereof.

In another embodiment, the carrier comprises oleoylpolyethylene glycol glyceride, linoleoylglycol glycol glyceride, lauroyl polyglycol glyceride, liquid paraffin, light liquid paraffin, soft paraffin (petrolatum), hard paraffin, wax, castor oil, peanut oil, sesame oil, medium chain triglycerides, cetearyl alcohol, lanolin, glycerol, propylene glycol, polyethylene glycol (PEG), or water.

Pharmaceutical Composition

The disclosure also provides a pharmaceutical composition for treating an ocular disease, comprising nintedanib, or its salt, derivative, analog, polymorph, or combination thereof. In one embodiment, the pharmaceutical composition comprises, alternatively consists essentially of, or yet consists of 0.01 mg/mL to 20 mg/mL, 0.1 mg/mL to 5 mg/mL, 0.5 mg/mL to about 4 mg/mL, 1 mg/mL to 4 mg/mL, 2 mg/mL to 3 mg/mL nintedanib, or its salt, derivative, analog or polymorph, or combination thereof. In one embodiment, the pharmaceutical composition comprises about 1 mg/mL to about 4 mg/mL comprises nintedanib, or its salt, derivative, analog or polymorph, or combination thereof. In another embodiment, the pharmaceutical composition comprises about 1 mg/mL to about 3 mg/mL nintedanib, or its salt, derivative, analog or polymorph, or combination thereof. In another embodiment, the pharmaceutical composition comprises, at least 0.01 mg/mL, 0.1 mg/mL, 0.5 mg/mL, 1 mg/mL, 5 mg/mL, 10 mg/mL, 15 mg/mL, 25 mg/mL, 50 mg/mL, or 100 mg/mL nintedanib, or its salt, derivative, analog or polymorph, or combination thereof. In another aspect, the concentration of nintedanib (or its salt, derivative, analog or polymorph) in the pharmaceutical composition is at least 0.001% w/v, 0.01% w/v, 0.1% w/v, 1% w/v, 5% w/v, or 10% w/v, 15% w/v, 20% w/v, 30% w/v, 40% w/v, or 50% w/v. In another embodiment, the concentration is from 0.001% w/v to 50% w/v, 0.001% w/v to 30% w/v, from 0.01% w/v to 20% w/v, 0.01% w/v to 10% w/v, from 0.1% w/v to 10% w/v, or from 1% w/v to 5% w/v.

In some embodiments, the nintedanib salt is nintedanib ethanesulfonate. In one embodiment, the pharmaceutical composition comprises 0.01 mg/mL to 20 mg/mL, 0.1 mg/mL to 5 mg/mL, 0.5 mg/mL to about 4 mg/mL, 1 mg/mL to 4 mg/mL, 2 mg/mL to 3 mg/mL nintedanib ethanesulfonate. In another embodiment, the pharmaceutical composition comprises, at least 0.01 mg/mL, 0.1 mg/mL, 0.5 mg/mL, 1 mg/mL, 5 mg/mL, 10 mg/mL, 15 mg/mL, 25 mg/mL, 50 mg/mL, or 100 mg/mL nintedanib ethanesulfonate. In one embodiment, the pharmaceutical composition comprises about 1 mg/mL nintedanib ethanesulfonate. In another embodiment, the pharmaceutical composition comprises about 5 mg/mL nintedanib ethanesulfonate.

The pharmaceutical composition may be used as an eye drop, an oculentum, a collyrium, an ointment, a lysosome, a gel, a liquid, a liposome, a microcapsule, a microsphere, or an intraocular injection.

The pH value of the pharmaceutical composition may vary depending on the active ingredient, other ingredient, temperature, and many surrounding conditions. On the other hand, the pH values may affect therapeutic efficacy of active ingredients in a pharmaceutical composition. In some embodiments, the pharmaceutical composition has a pH value ranging from 5 to 9. In another embodiment, the pharmaceutical composition has a pH value ranging from 6.5 to 7.5. In one embodiment, the pharmaceutical composition has a pH value of 6.8. In another embodiment, the pharmaceutical composition has a pH value of 7.5.

In another embodiment, the pharmaceutical composition further comprises an AMD therapeutic agent. In one embodiment, the AMD therapeutic agent comprises a VEGF inhibitor, a PDGF inhibitor, or an FGF inhibitor. In some embodiments, the AMD therapeutic agent comprises, alternatively consists essentially of, or yet consists of E10030, sirolimus, infliximab, POT-4, JSM6427, volociximab, ALG-1001, ATG003, AdPEDF.11, methotrexate, triple combination therapy (verteporfin-ranibizumab-dexamethasone).

In some embodiments, the pharmaceutical composition further comprises an angiogenesis inhibitor. Non-limiting angiogenesis inhibitors include squalamine, squalamine lactate (Evizon™, Genaear Corp.), and curcumin; Vascular endothelial growth factor (VEGF) inhibitors including pegaptanib (Macugen®, Eyetech/Pfizer), bevacizumab (Avastin®, Genentech, Inc.), concentrated shark cartilage extract (Neovastat®, Eterna Zentaris), PTK 787 (vatalanib, Schering AG/Novartis), ribozyme anti-angiogenic (Angiozyme®, Sirma Therapeutics, Inc./Chiron Corp.); AZD 6474 (Zactima®, AstraZeneca AB Ltd.), anti-angiogenesis chimeric monoclonal antibody specific VEGF receptor 2 (IMC-1C11, ImClone Sys. Inc.), isocoumarin 2-(8-hydroxy-6-methoxy-1-oxo-1H-2-benzopyran-3-yl) propionic acid (NM-3, Ilex Oncology Inc.), SU668 (Pfizer), isopropoxymethyl-12-(3-hydroxypropyl) ideno[2,1-a]pyrro[3,4-c]carbazol e-5-one (CEP-5214, Cephalon), CEP-7055 (the N,N-dimethyl glycine ester prodrug of CEP-5214, Cephalon), and PTC299 (PTC Therapeutics); Integrin antagonists such as anti-αvβ3 antibody (Vitaxin®, Medimmune Inc.); RDG peptide mimetics such as S137 and S247 (Pfizer), conformationally constrained bicyclic lactam Arg-Gly-Asp-containing pseudopeptides such as ST1646 (Sigma Tau S.p.A.); DPC A803350 (Bristol-Myers Squibb), and o-guanidines (3D Pharmaceuticals Inc.); matrix metalloproteinase inhibitors such as prinomastat (AG 3340, Pfizer), (ISV-616, InSite Vision), (TIMP-3, NIH); S3304 (Shionogi); BMS 275291 (Celltech/Bristol-Myers Squibb); SC 77964 (Pfizer); ranibizumab (Lucentis®, Genentech, Inc.); ABT 518 (Abbott Labs.); CV 247 (Ivy Medical); NX-278-L anti-VEGF aptamer (EyeTech Pharm.); 2'-O-mrthoxyethyl antisense C-raf oncogene inhibitor (ISIS-13650, Isis Pharm., Inc./iCo Therapeutics, Inc.); vitronectin and osteopontin antagonists (3D Pharm.); combretastatin A-4 phosphate (CA4P, Oxi-Gene, Inc.); fab fragment α-V/β-1 integrin antagonist (Eos-200-F, Protein Design Labs); α-v/β-3 integrin antagonist (Abbott Labs.); urokinase plasminogen activator fragment (A6, Angstrom Pharm.); VEGF antagonists (including AAV-PEDF, Chiron Corp.; VEGF-R, Johnson & Johnson/Celltech; SU10944, Sugen/Pfizer; VEGF-TRAP, Regeneron; SP-(V5.2)C, Supratek Pharm. Inc.; endostatin VEGF antagonist, EntreMed, Inc. (Rockville, Md.); kdr tyrosine kinase inhibitor (EG-3306, Ark Therapeutics); cytochalasin E (NIH); kallikrein-binding protein (Medical Univ., SC); combretastatin analog (MV-5-40, Tulane); pigment-epithelium derived growth factor (Med. Univ. SC); AdPEDF, GenVec, Inc.); plasminogen kringle (Medical Univ. SC);

rapamycin; cytokine synthesis inhibitor/p38 mitogen-activated protein kinase inhibitor (SB-220025, GlaxoSmithKline); FGF1 receptor antagonist/tyrosine kinase inhibitor (Pfizer/Sugen); bradykinin B1 receptor antagonist (B-9858, Cortech, Inc.); bactericidal/permeability-increasing protein (Neuprex®, Xoma Ltd.); protein kinase C inhibitor (Hypericin, Sigma-Aldrich, St. Louis, Mo.); ruboxistaurin mesylate (LY-333531, Eli Lilly & Co.); polysulphonic acid derivatives (Fuji Photo Film); growth factor antagonists such as TBC-2653 and TBC-3685 (Texas Biotech. Corp.); Tunica internal endothelial cell kinase (Amgen Inc.)

The formulations according to the present invention have particular applicability in providing a controlled and sustained release of active agents effective in obtaining a desired local or systemic physiological or pharmacological effect relating at least to the treatment of ocular diseases (e.g., AMD and CNV). In one embodiment, the pharmaceutical composition comprises a sustained-release intraocular implant, a matrix preparation, a capsule preparation, or combination thereof. In some embodiments, the sustained-release intraocular implant comprises hydroxypropylcellulose, hydroxypropylmethylcellulose, hydroxypropylmethylcellulose phthalate, pullulan, gelatin, collagen, atelocollagen, hyaluronic acid, casein, agar, acacia, dextrin, ethylcellulose, methylcellulose, chitin, chitosan, mannan, carboxymethylethylcellulose, sodium carboxymethylcellulose, polyethylene glycol, sodium alginate, polyvinyl alcohol, cellulose acetate, polyvinylpyrrolidone, polysiloxane, polyvinyl acetal diethylaminoacetate, albumin, lactic acid-glycolic acid copolymers, or combination thereof.

In some embodiments, the pharmaceutical composition comprises a pharmaceutically acceptable carrier or excipient. In one embodiment, the excipient comprises a surfactant, a gelling agent, an organic co-solvent preservative, a fungicide or an antibacterial agent, a pH adjuster, an isotonic agent, a chelating agent, a buffer, a stabilizer, an antioxidant, a thickener, or combination thereof. In another embodiment, the carrier comprises oleoylpolyethylene glycol glyceride, linoleoylglycol glycol glyceride, lauroyl polyglycol glyceride, liquid paraffin, light liquid paraffin, soft paraffin (petrolatum), hard paraffin, wax, castor oil, peanut oil, sesame oil, medium chain triglycerides, cetearyl alcohol, lanolin, glycerol, propylene glycol, polyethylene glycol (PEG), or water.

In another embodiment, the pharmaceutical composition comprises liquid paraffin, anhydrous lanolin, benzalkonium chloride, Vaseline, anhydrous lanolin, soybean lecithin, cholesterol, triglyceride, polyoxyethylene castor oil, glycerin, vitamin E, Tween 80, or combination thereof. In one embodiment, the triglyceride is a medium chain triglyceride.

In one embodiment, the pharmaceutical composition further comprises a binding agent, a flavor agent, a lubricating agent, a flow agent, a disintegration agent, a delay agent, or combination thereof.

The pharmaceutical composition of the disclosure may be used for treating various types of ocular diseases. In one embodiment, the ocular diseases comprise age-related macular degeneration ("AMD"), choroidal neovascularization ("CNV"), retinal detachment, diabetic retinopathy, atrophy of retinal pigment epithelium, hypertrophy of retinal pigment epithelium, retinal vein occlusion, choroidal retinal vein occlusion, macular edema, anterior angiogenesis, cornea angiogenesis, pterygium conjunctiva, sub-retinal edema, choroidal neovascularization, cystoid macular edema, epiretinal membrane, macular hole, vascular streaks, pigmented retinitis, Stuttgart disease, glaucoma, cataract, inflammatory condition, refractory abnormalities, conical cornea, retinopathy of prematurity, retinal edema, or high myopia. In one embodiment, the ocular disease is AMD. In another embodiment, the ocular disease is CNV.

Eye Drop Formulation or Topical Ophthalmic Formulation

The disclosure also provides a pharmaceutical eye drop formulation or a topical ophthalmic formulation that comprises nintedanib, or its salt, derivative, analog, solvate, hydrate, or polymorph, or combination thereof.

The amount of nintedanib (or its salt, derivative, analog, solvate, hydrate, or polymorph) in the eye drop formulation may range between 0.01% w/v to 10% w/v, 0.3% w/v to 5% w/v, 0.5% w/v to 1% w/v, or 0.5% w/v. Other percentages include 0.1% w/v, 0.15% w/v, 0.2% w/v, 0.3% w/v, 0.4% w/v, 0.5% w/v, 0.6% w/v, 0.7% w/v, 0.8% w/v, 0.9% w/v, 1.0% w/v, 1.5% w/v, 2% w/v, 3% w/v, 3.5% w/v, 4% w/v, and 5% w/v. The percentage, in another embodiment, is 0.001% w/v, 0.01% w/v, 0.1% w/v, 1% w/v, 5% w/v, or 10% w/v, 15% w/v, 20% w/v, 30% w/v, 40% w/v, or 50% w/v. In some embodiments, the nintedanib salt is nintedanib ethanesulfonate.

Benzethonium chloride or benzalkonium chloride used in this disclosure has a bactericidal action which can prevent any contamination of the eye drop with microorganisms during using the same. The amount of benzalkonium chloride in the eye drop formulation may range between 0.01% w/v to 10% w/v, preferably 0.05% w/v to 4% w/v, more preferably 0.1% w/v to 1% w/v, and most preferably 0.1% w/v to 0.15% w/v. Other percentages include 0.01% w/v, 0.02% w/v, 0.03% w/v, 0.04% w/v, 0.05% w/v, 0.06% w/v, 0.07% w/v, 0.08% w/v, 0.09% w/v, 0.1% w/v, 0.125% w/v, 0.15% w/v, 0.2% w/v, 0.3% w/v, 0.4% w/v, 0.5% w/v, 0.6% w/v, 0.7% w/v, 0.8% w/v, 0.9% w/v, 1.0% w/v, 1.5% w/v, 2% w/v, 3% w/v, 3.5% w/v, 4% w/v, and 5% w/v.

In some embodiments, the eye drop formulation comprises 1 to 20 mg/mL nintedanib ethanesulfonate, 50 to 200 mg/mL medium chain triglyceride, 5 to 30 mg/mL soybean lecithin, 2 to 20 mg/mL cholesterol, 5 to 50 mg/mL glycerin, 0.05 to 0.5 mg/mL benzalkonium chloride, and 0.1 to 1 mg/mL vitamin E. In another embodiment, the formulation comprises 7 to 15 mg/mL nintedanib ethanesulfonate, 100 to 200 mg/mL medium chain triglyceride, 10 to 20 mg/mL soybean lecithin, 2 to 6 mg/mL cholesterol, 15 to 30 mg/mL glycerin, 0.05 to 0.2 mg/mL benzalkonium chloride, and 0.2 to 0.5 mg/mL vitamin E. In another embodiment, the eye drop formulation comprises 0.1 to 100 mg/mL, 1 to 50 mg/mL, 2 to 20 mg/mL, or 5 to 15 mg/mL nintedanib ethanesulfonate. In another embodiment, the eye drop formulation comprises 1 to 20 mg/mL, 2 to 15 mg/mL, or 5 to 12 mg/mL nintedanib ethanesulfonate. In a preferred embodiment, the formulation comprises 10 mg/mL nintedanib ethanesulfonate, 150 mg/mL medium chain triglyceride, 15 mg/mL soybean lecithin, 4 mg/mL cholesterol, 20 mg/mL glycerin, 0.1 mg/mL benzalkonium chloride, and 0.3 mg/mL vitamin E. In another embodiment, the pharmaceutical formulation comprises 10 mg/mL nintedanib ethanesulfonate.

In one embodiment, the pharmaceutical eye drop formulation further comprises Tween 80 or polyoxyethylene castor oil. In another embodiment, the formulation is in the form of an oculentum, a collyrium, a liposome, a microcapsule, microsphere, or an intraocular injection.

Ophthalmic ointments tend to keep an active agent in contact with the eye longer than suspensions and certainly solutions. In some instance, ointments tend to blur vision, as they are not removed easily by the tear fluid. In some embodiment, ointments are used at night as adjunctive therapy to eye drops used during the day. In one embodiment, the ointment is used during the day. The ointment of this disclosure, in one embodiment, comprises nintedanib, or its salt, derivative, analog, solvate, hydrate, or polymorph.

The pH value in the pharmaceutical formulation ranges from 5 to 9. In one embodiment, the pH value ranges from 6.5 to 7.5. In another embodiment, a pH value ranges from 5 to 9.

Sterility is important for ophthalmic formulations. Contaminated formulations may result in eye infections that can aggravate the existing ocular diseases, or cause new diseases. The contamination could ultimately cause blindness, especially when the *P. aeruginosa* microbe is involved. Therefore, ophthalmic formulations as described herein, in some embodiments, are prepared using techniques, unique for solutions, gels, suspensions and ointments of the inventive compositions that assure sterility. Sterile formulations is packaged in sterile containers. Most topical ophthalmic products are typically packaged in multidose form. As such preservatives can prevent microbial contamination of an otherwise sterile product during use. Non-limiting examples of suitable preservatives for the eye drop formulation include quaternary ammonium compounds (salts), such as benzalkonium chloride, benzethonium chloride, cetalkonium chloride, cetrimide, benzododecinium bromide and benzoxonium chloride; Alkyl-mercury salts of thiosalicylic acid, such as thimerosal; Parabens, such as methylparaben and propylparaben; chelating agents, such as disodium edetate, sodium gluconate, sodium propionate; other agents, such as chlorobutanol, boric acid, sorbic acid, phenylethanol; Purite® chlorine dioxide; Polyquad® polyquatemium-1; and Aldox® myristamidopropyl diethylamine; or other agents known to those skilled in the art.

In some embodiments, the pharmaceutical formulation further comprises a sustained-release intraocular implant, a matrix preparation, a capsule preparation, or combination thereof. In one embodiment, the sustained-release intraocular implant comprises hydroxypropylcellulose, hydroxypropylmethylcellulose, hydroxypropylmethylcellulose phthalate, pullulan, gelatin, collagen, atelocollagen, hyaluronic acid, casein, agar, acacia, dextrin, ethylcellulose, methylcellulose, chitin, chitosan, mannan, carboxymethylethylcellulose, sodium carboxymethylcellulose, polyethylene glycol, sodium alginate, polyvinyl alcohol, cellulose acetate, polyvinylpyrrolidone, polysiloxane, polyvinyl acetal diethylaminoacetate, albumin, lactic acid-glycolic acid copolymers, or combination thereof.

In one embodiment, the pharmaceutical formulation further comprises a pharmaceutically acceptable carrier or excipient. The excipient, in one embodiment, comprises a surfactant, a gelling agent, an organic co-solvent preservative, a fungicide or an antibacterial agent, a pH adjuster, an isotonic agent, a chelating agent, a buffer, a stabilizer, an antioxidant, a thickener, or combination thereof. The carrier, in another embodiment, comprises oleoylpolyethylene glycol glyceride, linoleoylglycol glycol glyceride, lauroyl polyglycol glyceride, liquid paraffin, light liquid paraffin, soft paraffin (petrolatum), hard paraffin, wax, castor oil, peanut oil, sesame oil, medium chain triglycerides, cetearyl alcohol, lanolin, glycerol, propylene glycol, polyethylene glycol (PEG), or water.

The pharmaceutical formulation of claim, in some embodiments, further comprises liquid paraffin, anhydrous lanolin, benzalkonium chloride, Vaseline, anhydrous lanolin, soybean lecithin, cholesterol, triglyceride, polyoxyethylene castor oil, glycerin, vitamin E, Tween 80, or combination thereof. The pharmaceutical formulation, in one embodiment, comprises a binding agent, a flavor agent, a lubricating agent, a flow agent, a disintegration agent, a delay agent, or combination thereof.

The pharmaceutical composition or formulation comprises one or more units of formulation. The weight of the active ingredient contained in each unit formulation is n times the effective dose of the active ingredient, wherein n is a number between 0.1 and 1, preferably, n is 1. In one embodiment, when the drug is an eye drop, the single unit preparation formulation means one drop. When the drug is an oculentum, the one unit preparation formulation is 1 cm length of the paste. When the drug is a collyrium, the one unit formulation refers to the amount of 5 ml. When the drug is liposomes, microcapsules, microspheres or intraocular injections, the one unit formulation refers to an injection volume of 0.05 mL.

In some embodiments, the effective therapeutic dose of the active ingredient (e.g., nintedanib, or its salt, derivative, analog, solvate, hydrate, or polymorph) in the pharmaceutical composition is 0.1 to 25 µg/time/eye. In one embodiment, the effective therapeutic dose of the active ingredient (e.g., nintedanib, or its salt, derivative, analog, solvate, hydrate, or polymorph) in the pharmaceutical composition is 0.5 to 25 µg/time/eye. In another embodiment, the effective therapeutic dose of the active ingredient (e.g., nintedanib, or its salt, derivative, analog, solvate, hydrate, or polymorph) in the pharmaceutical composition is 2.5 to 10 µg/time/eye. In another embodiment, the effective therapeutic dose of the active ingredient (e.g., nintedanib, or its salt, derivative, analog, solvate, hydrate, or polymorph) in the pharmaceutical composition is 2.5 to 5 µg/time/eye.

Due to the implementation of the above technical schemes, the present invention has at least the following advantages. In the experimental study, Nintedanib and its salt or solvate have been found to have a significant therapeutic effect on ocular diseases such as choroidal neovascularization, and the eye drops showed better activity and showed good safety and effect at a broad range of doses (e.g., 0.1 to 25 µg/time/eye).

The eye drop of the present invention may comprise other components usually used in eye drops in addition to the foregoing components insofar as the object of the present invention is not impaired. Such other additives include, for instance, a buffering agent, an isotonicity, a surfactant and a chelating agent. Examples of buffering agents are phosphoric acid salts, boric acid salts and organic bases. Examples of isotonicities include sodium chloride, potassium chloride, boric acid and sodium borate. Examples of surfactants are polysorbate 80 and polyoxyethylene-hydrogenated castor oil 60.

Process of Preparing a Pharmaceutical Composition

In addition, the disclosure relates to methods of preparing a pharmaceutical formulation suitable for administering to a subject in need thereof. The method of preparing the pharmaceutical composition is also disclosed in CN App. No. 20151 0908457.7, which is incorporated by reference in its entirety.

The method comprises: micronizing a composition comprising nintedanib, or its salt, derivative, analog or polymorph, or combination thereof; mixing the micronized composition with other ingredients; and sonicating the mixture. In some embodiments, the pharmaceutical composition forms an emulsion.

The composition, which comprises nintedanib, or its salt, derivative, analog or polymorph, or combination thereof, is micronized to form the embodiment of this disclosure. Micronization can be accomplished in any manner known to one of skill in the art for particle size reduction. Non-limiting example of micronization include ball micronizing; media micronizing; fluidized bed jet micronizing; spiral jet micronizing; air classifying micronizing; universal pin micronizing; hammer and screen micronizing; attrition micronizing; cone micronizing; and/or granulating.

In one embodiment, the average particle size of the micronized composition is between about 5 μm and about 200 μm. In another embodiment, the average particle size is at least about 5 μm. In another embodiment, the average particle size is at least about 10 μm. In another embodiment, the average particle size of the base granular starch is between about 5 μm and about 20 μm. In another embodiment, the average particle size of the base granular starch is between about 5 μm and about 100 μm. In another embodiment, the mean average particle size of the micronized composition is between about 2 μm and about 4 μm. In another embodiment, the average particle size is less than about 3 μm. In another embodiment, the average particle size is less than about 2 μm. In another embodiment, the average particle size is less than about 1 μm.

In some embodiments, the method further comprises filtering the mixture or the emulsion. In one embodiment, the method comprises evaporating the emulsion to obtain a homogenous liposome suspension.

In some embodiments, the liposome suspension is homogenous. In another embodiment, the methods prepares the pharmaceutical formulation as an eye drop, an oculentum, a collyrium, an ointment, a lysosome, a gel, a liquid, a liposome, a microcapsule, a microsphere, or an intraocular injection.

In some embodiments, the other ingredients comprise liquid paraffin, anhydrous lanolin, benzalkonium chloride, Vaseline, anhydrous lanolin, soybean lecithin, cholesterol, triglyceride, polyoxyethylene castor oil, glycerin, vitamin E, Tween 80, or combination thereof. In one embodiment, the other ingredients comprise a sustained-release intraocular implant, a matrix preparation, a capsule preparation, or a combination thereof.

The method, in one embodiment, comprises adjusting the pH value between about 5 and about 9. In one embodiment, the pH value is adjusted between about 6.5 and about 7.5.

The method for preparing the pharmaceutical composition (e.g., eye drops), comprises mixing solution A with solution B; adjusting the pH value; and emulsifying the mixture of said solution A and said solution B, wherein said solution A comprises medium chain triglycerides, soybean lecithin, glycerol, cholesterol, and a surfactant (e.g., Tween 80 or polyoxyethylene castor oil), nintedanib (or its salt, derivative, analog, solvate, hydrate, or polymorph, e.g., nintedanib ethanesulfonate), and solution B comprises vitamin E, benzalkonium chloride (or benzalkonium bromide), and a surfactant (e.g., Tween 80 or polyoxyethylene castor oil) with water.

In one embodiment, the surfactant comprises polysorbate 80, polyoxyethylene castor oil 60, polyoxyethylene hydrogenated castor oil 60, polyethylene glycol stearate, polyethylene glycol, lecithin, sucrose esters, polyoxyethylene fatty alcohol ethers, poloxamers, tyloxapol (Tyloxapol), Tween 80 or combination thereof. In another embodiment, the surfactant comprises Tween 80 or polyoxyethylene castor oil.

In some embodiments, the nintedanib (or its salt, derivative, analog, solvate, hydrate, or polymorph, e.g., nintedanib ethanesulfonate) is micronized. As disclosed in other part of this application, micronization can be accomplished in any manner known to one of skill in the art for particle size reduction. Non-limiting example of micronization include ball micronizing; media micronizing; fluidized bed jet micronizing; spiral jet micronizing; air classifying micronizing; universal pin micronizing; hammer and screen micronizing; attrition micronizing; cone micronizing; and/or granulating.

The emulsified mixture can be further sterilized. In one embodiment, the mixture is sterilized with moist heat. The temperature of moist heat is least 100° C., 120° C., 140° C., 160° C., 180° C., or 200° C. In some embodiments, the moist heat is at least 120° C. In one embodiment, the moist heat is 121° C. The sterilization period can be at least 1 minute, 5 minutes, 10 minutes, 30 minutes, 50 minutes, 60 minutes, or 100 minutes. In some embodiments, the mixture is sterilized for 30 minutes.

In some embodiments, solution A is made by (1) heating and stirring to mix the medium chain triglycerides, soybean lecithin, glycerol with a surfactant (e.g., Tween 80 or polyoxyethylene castor oil); (2) adding cholesterol; (3) filtering the mixture to provide; and (4) dissolving nintedanib (or its salt, derivative, analog, solvate, hydrate, or polymorph, e.g., nintedanib ethanesulfonate) in the solution.

In one embodiment, solution B is made by (1) mixing vitamin E, benzalkonium chloride (or benzalkonium bromide) with a surfactant (polyoxyethylene castor oil or Tween 80) in water; (2) filtering this mixture in water; and (3) emulsifying the mixture.

In one embodiment, the mixture is emulsified by homogenizer. The speed of homogenizeris 100 rpm, 200 rpm, 300 rpm, 400 rpm, 500 rpm, 600 rpm, 700 rpm, 800 rpm, 900 rpm, 1,000 rpm, 2,000 rpm, 3,000 rpm, 4,000 rpm, 5,000 rpm, 6,000 rpm, 7,000 rpm, 8,000 rpm, 9,000 rpm, 10,000 rpm, 20,000 rpm, 30,000 rpm, or 40,000 rpm. The homogenizerperiod is at least 1 minute, 5 minutes, 10 minutes, 20 minutes, 40 minutes, 60 minutes, 100 minutes, 200 minutes, 500 minutes, or 1,000 minutes.

In one embodiment, the pH value is adjusted to 5 to 9, 6 to 8, or 6.5 to 7.5. In another embodiment, the pH value is adjusted to 6.5 to 7.5.

WORKING EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1 Preparation of Nintedanib Ethanesulfonate Oculentum

The nintedanib ethanesulfonate oculentum was prepared in a C-level clean area with clean bench (e.g., sterile cabinet). In the preparation, a mixture containing micronized powder of nintedanib ethanesulfonate and benzalkonium chloride were added to an appropriate container.

The mixture was then sterilized, filtered, and cooled before liquid paraffin was added. Once the paraffin became solid, the mixture was grounded to fine paste, sifted through a No. 6 sieve, gradually added to the filtered, sterilized lanolin and Vaseline matrix, and then stirred to mix uniformly before the mixture cooled down.

In every 100 g nintedanib ethanesulfonate oculentum, the preparation contained 1 g nintedanib ethanesulfonate, 10 g liquid paraffin, 10 g anhydrous lanolin, and 0.01 g benzalkonium chloride. The remaining ingredient is Vaseline.

Example 2 Preparation of Nintedanib Ethanesulfonate Liposomal Eye Drops

The nintedanib ethanesulfonate liposomal eye drops were prepared in a C-level clean area with clean bench (e.g., sterile cabinet). In the preparation, an oil phase was prepared with a mixture containing micronized powder of nintedanib ethanesulfonate, soybean lecithin, cholesterol, and benzalkonium chloride that were dissolved in 10 mL of ether aseptically. The water phase was prepared with 10 mL of 0.9% sodium chloride solution, with hydrochloric acid or sodium hydroxide with the pH adjusted to 6.8.

The two phases were mixed and intermittently sonicated for 30 minutes until a stable water/oil (W/O) emulsion was formed. The emulsion was evaporated on a rotary evaporator to remove the organic solvent (water bath temperature: 30° C., rotation speed: 75 rpm). After the gel was formed on the flask wall, rotary evaporation continued to allow the gel to fall off and to be hydrated to provide a uniform liposome suspension. The suspension was sterilized by filtration through a 0.45 μm microporous membrane and stored at 4° C.

The prepared nintedanib ethanesulfonate liposomal eye drop solution approximately contains 0.2 g nintedanib ethanesulfonate, 1 g soybean lecithin, 0.4 g cholesterol, and 0.002 g benzalkonium chloride.

Example 3 Preparation of Nintedanib Ethanesulfonate Emulsion Eye Drops

In a C-level clean area with clean bench (e.g., sterile cabinet), medium chain triglycerides, soybean lecithin, glycerin, and half of polyoxyethylene castor oil were heated and stirred to mix. Cholesterol was then dissolved in the mixture, which was filtered to form an oil phase. Micronized nintedanib Ethanesulfonate was dissolved in the oil phase under and aseptic condition. Vitamin E, benzalkonium chloride, and another half of polyoxyethylene castor oil were added in water and filtered to form the aqueous-phase the solution. The water phase was homogenously emulsified at 1,000 rpm for 10 minutes before the oil phase was quickly added to the water phase.

Hydrochloric acid or sodium hydroxide was used to adjust the pH to 7.5 and osmotic pressure. The solution was homogenously emulsified at 3000 rpm for 30 minutes, sterilely aliquoted into eye drops container and sterilized with moist heat (121° C., 30 minutes). Water was added to make a 100 ml solution, which contains 1 g nintedanib ethanesulfonate, 15 g medium chain triglycerides, 0.1 g polyoxyethylene castor oil, 1.5 g soybean lecithin, 0.4 g cholesterol, 2 g glycerin, 0.01 g benzalkonium chloride, and 0.03 g vitamin E.

Example 4 Preparation of Nintedanib Ethanesulfonate Emulsion Eye Drops

In a C-level clean area with clean bench (e.g., sterile cabinet), medium chain triglycerides, soybean lecithin, glycerin, and half of Tween 80 were heated and stirred to mix. Cholesterol was then dissolved in the mixture, which was filtered to form an oil phase. Micronized nintedanib Ethanesulfonate was dissolved in the oil phase under an aseptic condition. Vitamin E, benzalkonium chloride, and another half of Tween 80 oil were added in water and filtered to form the aqueous-phase the solution. The water phase was homogeneously emulsified at 1,000 rpm for 10 minutes before the oil phase was quickly added to the water phase.

Hydrochloric acid or sodium hydroxide was used to adjust the pH to 6.8 and osmotic pressure. The solution was homogeneously emulsified at 3000 rpm for 30 minutes, sterilely aliquoted into eye drops container and sterilized with moist heat (121° C., 30 minutes). Water was added to make 100 ml solution, which contains 1 g nintedanib ethanesulfonate, 15 g medium chain triglycerides, 0.1 g Tween 80, 1.5 g soybean lecithin, 0.4 g cholesterol, 2 g glycerin, 0.01 g benzalkonium chloride, and 0.03 g vitamin E.

Example 5 Preparation of Nintedanib Ethanesulfonate Emulsion Eye Drops

In a C-level clean area with clean bench (e.g., sterile cabinet), medium chain triglycerides, soybean lecithin, glycerin, and half of polyoxyethylene castor oil were heated and stirred to mix. Cholesterol was then dissolved in the mixture, and then filtered to form an oil phase. Micronized nintedanib Ethanesulfonate was dissolved in the oil phase under and aseptic condition. Vitamin E, benzalkonium chloride, and another half of polyoxyethylene castor oil were added in water and filtered to form the aqueous-phase the solution. The water phase was homogeneously emulsified at 1,000 rpm for 10 minutes before the oil phase was quickly added to the water phase.

Hydrochloric acid or sodium hydroxide was used to adjust the pH (to 6.5) and osmotic pressure. The solution was homogeneously emulsified at 3000 rpm for 30 minutes, sterilely aliquoted into eye drops container and sterilized with moist heat (121° C., 30 minutes).

Water was added to make 100 ml solution, which contains 1 g nintedanib ethanesulfonate, 15 g medium chain triglycerides, 0.1 g polyoxyethylene castor oil, 1.5 g soybean lecithin, 0.4 g cholesterol, 2 g glycerin, 0.01 g benzalkonium chloride, and 0.03 g vitamin E.

The pH, osmolality osmotic pressure, viscosity, clarity detection and average particle size of the nintedanib ethanesulfonate emulsion type eye drops prepared in Examples 3 to 5 were measured with the accelerated test. The results are shown in Table 1.

TABLE 1

Test Results for Emulsion Type Eye Drops

| | Example 3 | Example 4 | Example 5 |
|---|---|---|---|
| pH | 7.5 | 6.8 | 6.5 |
| Osmolality (mOsm) | 290 | 270 | 270 |
| Viscosity (cPa · s) | 4.43 | 4.08 | 3.90 |
| Clarity | No visible foreign matter | No visible foreig nmatter | No visible foreign matter |
| Average particle size (nm) | 422 | 380 | 475 |
| 0 day | Yellow emulsion | Yellow emulsion | Yellow emulsion |
| 40° C., RH 75% 5 days | Yellow emulsion | Yellow emulsion | Yellow emulsion |
| 40° C., RH 75% 10 days | Yellow emulsion | Yellow emulsion | Yellow emulsion |
| 40° C., RH 75% 30 days | Yellow emulsion | Yellow emulsion | Yellow emulsion |

Table 1 shows that the eye drop of the present invention had good stability in an accelerated test (40° C., RH 75%), and the pH, osmotic pressure, viscosity, clarity, and average particle size were in accordance with the requirements of eye drops.

Example 6 Nintedanib Ethanesulfonate Emulsion Eye Drop on Corneal Neovascularization in Rabbits 18 healthy New Zealand rabbits were weighed and anesthetized with 3% pentobarbital sodium (1 mL/kg). Local anesthetic lidocaine hydrochloride was administered on the surface of the eye at a dose of 20 µL/eye. 9 mm diameter filter paper was immersed in 1 mol/L sodium hydroxide solution for about 10 seconds, with tweezers. The filter paper was placed on dry filter paper to remove excess sodium hydroxide solution before it was laid at the center of the rabbit's cornea for 60 seconds. Then, the paper was removed and the cornea was immediately flushed with 20 mL of physiological saline using a washing bottle. Antibiotics were applied to prevent infection (chlortetracycline eye oculentum) for two times per day.

The rabbits, after modeling, were divided into five groups: 1) burn group, 2) Group A, which was treated with nintedanib ethanesulfonate emulsion drops (10 mg/mL, prepared as in Example 3), 3) Group B, which was treated with nintedanib ethanesulfonate emulsion eye drops (5 mg/mL prepared as in Example 3), and 4) Group C, which was treated with emulsion eye drops matrix without nintedanib ethanesulfonate (prepared as in Example 1).

The day of model building was counted as day 0, from which, Groups A, B, C were given the corresponding eye drops for 5 times/day and 50 µL/eye each time. The administration continued for 10 days. Additional two New Zealand rabbits were used as the normal group. At the same time of daily administration, growth of corneal neovascularization (NV) and other inflammatory responses in the eyes were observed.

On day 10 after applying the eye drops, the rabbits were anesthetized with 3% pentobarbital sodium (1 mL/kg). Local anesthetic lidocaine hydrochloride was administered at 20 µL/eye dose on the surface of the eyes. The development of corneal NV was observed with slit lamp under a 10× objective lens. The NVs were taken photos under 10 times and a 16× objective lens. The area of the cornea NV was processed with Image Pro Plus. The formula for calculating area is $S=C/12\times3.1416\times[R^2-(R-L)^2]$, in which C represents the number of clock hours of the limbus from NV growth to no NV growth in the picture, R represents the length between the limbus in contact with the sclera and the center of the cornea in the picture, and L represents the NV length between the root of NV in the limbus in contact with the sclera and the end of the NV in the cornea in the picture.

The longest blood vessel was also taken, and the data were analyzed by T test variance analysis. The data were expressed as $\bar{x}\pm s$, in which $\bar{x}$ is the mean, and s is the standard deviation. The results are shown in Table 2.

TABLE 2

Effects of Nintedanib Ethanesulfonate emulsion eye drops on alkali burns induced corneal neovascularization

| Group | The number of eyes | Dose (mg/mL) | Volume of administration (µL) | NV area (mm$^2$) |
|---|---|---|---|---|
| Normal | 4 | — | — | 0 |
| Burn | 8 | — | — | 35 ± 6.328 |
| A | 8 | 10 | 50 | 16 ± 9.889 |
| B | 8 | 5 | 50 | 24 ± 5.134 |
| C | 8 | 0 | 50 | 46 ± 26.436 |

Effects on corneal neovascular area: Day 10 corneal NV area data analysis results are shown in Table 2, compared with the alkali burn group treated with emulsion matrix without nintedanib Ethanesulfonate.

Treatment with nintedanib ethanesulfonate emulsion (5 mg/mL or 10 mg/mL) significantly ($P<0.05$) inhibited the corneal NV growth and reduced the NV area with 10 mg/mL of eye drops showing a better effect than 5 mg/mL. The emulsion matrix without nintedanib Ethanesulfonate did not inhibit the growth of corneal neovascularization and had an area of NV greater than that of the burn group.

Example 7 Nintedanib Ethanesulfonate Eye Drop on Corneal Neovascularization in Rats Specific-pathogen-free (SPF) grade Brown Norway (BN) rats, half male and half female, were treated with fundus laser photocoagulation, the date of which was counted as D0. At D8, 32 rats with similar areas of fluorescence leakage were selected, separated to 8 groups, with each group including 4 rats (half male and half female):

Group 1 is a model group without any treatment.

Group 2 is a positive control group, in which Conbercept was injected into the vitreous cavity of the rats' eyes at the dosage of 50 µg/eye and 6 times per day.

In group 3, both eyes of the rats were administered with nintedanib ethanesulfonate at the dosage of 125 µg/eye and 6 times per day from day 8 and day 15 (D8~D15).

In group 4, both eyes of the rats were administered with nintedanib ethanesulfonate at the dosage of 25 µg/eye and 6 times per day from day 8 and day 15 (D8~D15).

In group 5, both eyes of the rats were administered with nintedanib ethanesulfonate at the dosage of 5 µg/eye and 6 times per day from day 8 and day 15 (D8~D15).

In group 6, both eyes of the rats were administered with nintedanib ethanesulfonate at the dosage of 2.5 µg/eye and 6 times per day from day 8 and day 15 (D8~D15).

In group 7, both eyes of the rats were administered with nintedanib ethanesulfonate at the dosage of 0.5 µg/eye and 6 times per day from day 8 and day 15 (D8 D15).

In group 7, both eyes of the rats were administered with nintedanib ethanesulfonate at the dosage of 0.1 µg/eye and 6 times per day from day 8 and day 15 (D8 D15).

Figure 2A:
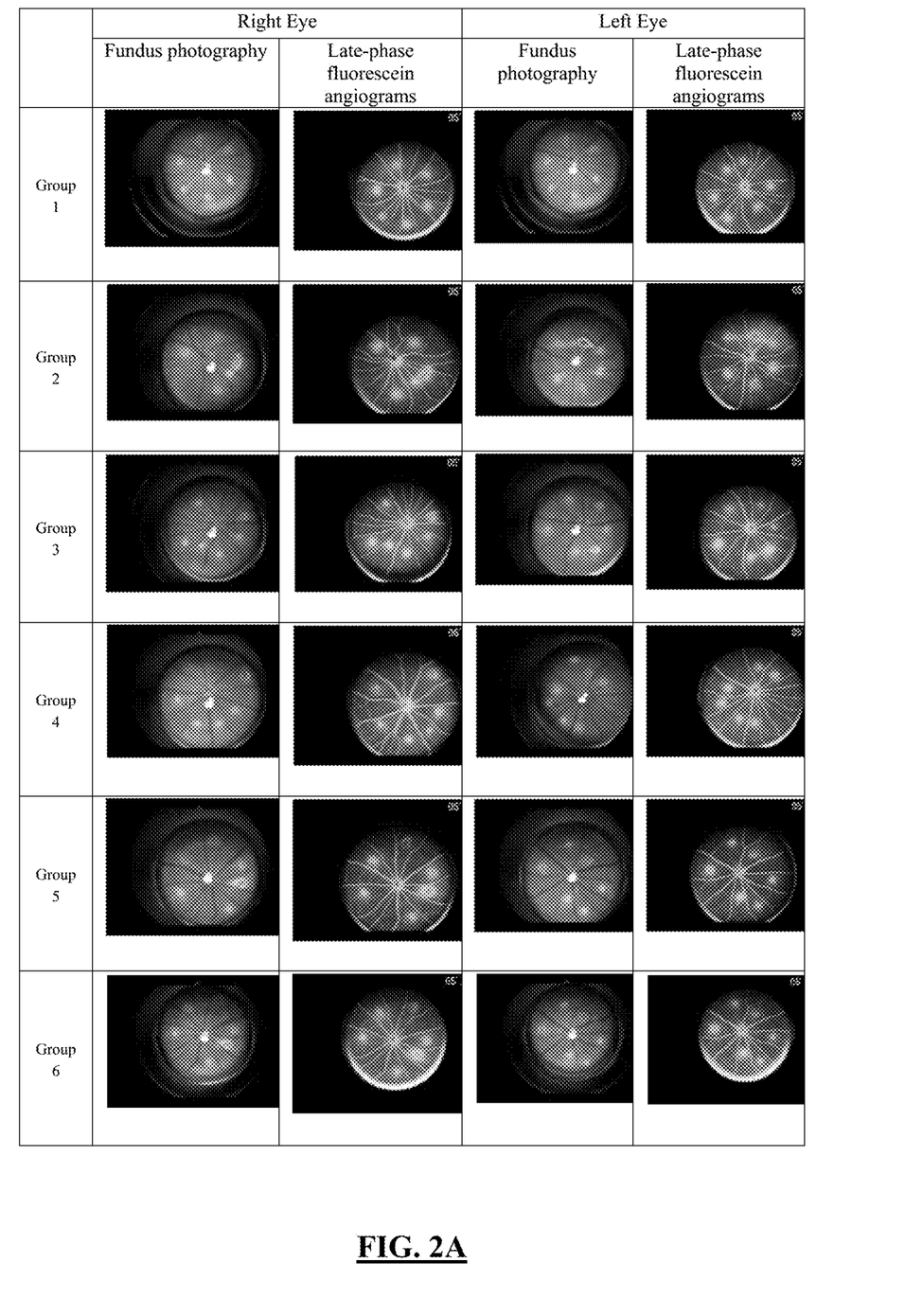
FIG. 2A and FIG. 2B show the pictures of fundus photography ("FP") and late-phase fluorescein angiography ("FFA") of experimental animals.
Figure 2B:
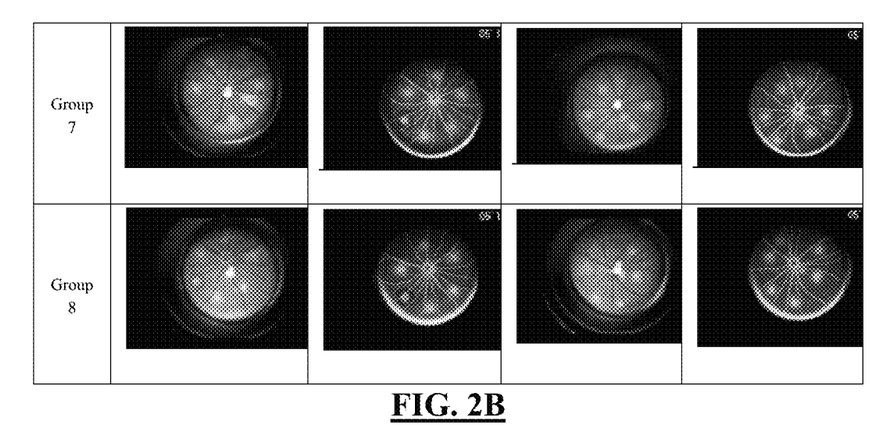

All rats were tested with fundus photography ("FP") and fundus fluorescein angiography ("FFA") one day before administration and 8 days after administration. The degree of CNV was graded according to the degree of fluorescence leakage. The results were used to evaluate the effect of nintedanib ethanesulfonate on rat CNV, the results of which are shown in FIG. 2.

Except some of the animals in groups 3 and 4 (corneal opacity), animals in other groups did not experience any significantly adverse reactions.

Ratio of Light Spots

One day before the administration, there was no significant difference in CNV lesion ratios between the model group and the other groups ($p>0.05$). The ratio is calculate by comparing the early-phase and last-phase fluorescein angiograms. The fluorescence leakage of the light spots was graded as follows: grade 0 (no leakage); grade 1 (slight leakage, leakage area is 1%-50% of the light spot size); grade 2 (moderate leakage, leakage area is 50%-100% of the light spot size); grade 3 (strong leakage, leakage area is larger than the light spot size). The ratios of light spots for certain grade were calculated as follows:

Ratio of light spot (%)=(the number of light spot at certain grade÷the sum of four kinds of light spots)×100.

After treatment, compared with the model group, the ratios of grade 3 light spots significantly decreased in the positive control group and in groups 3-6. The ratios of grade 1 light spots increased in groups 3-6. The ratios of grade 1 light spots of groups 3-6 increased ($p\leq0.05$). The results suggest that 1 week after photocoagulation, the treatment in groups 4-6 significantly inhibited the CNV in rats.

Compared to the positive control group, the ratios of grade 3 light spots of groups 3-6 were lower. The ratios of grade 1 light spots of all groups increased (the fifth group was significantly increased p≤0.05). There was no significant difference in the ratio of the level 0 and level 2 light spot between other groups (p>0.05). The result suggested that the inhibition of leakage was slightly stronger in the first group than that of the positive control group.

Mean Fluorescein Leakage Score

Figure 3:
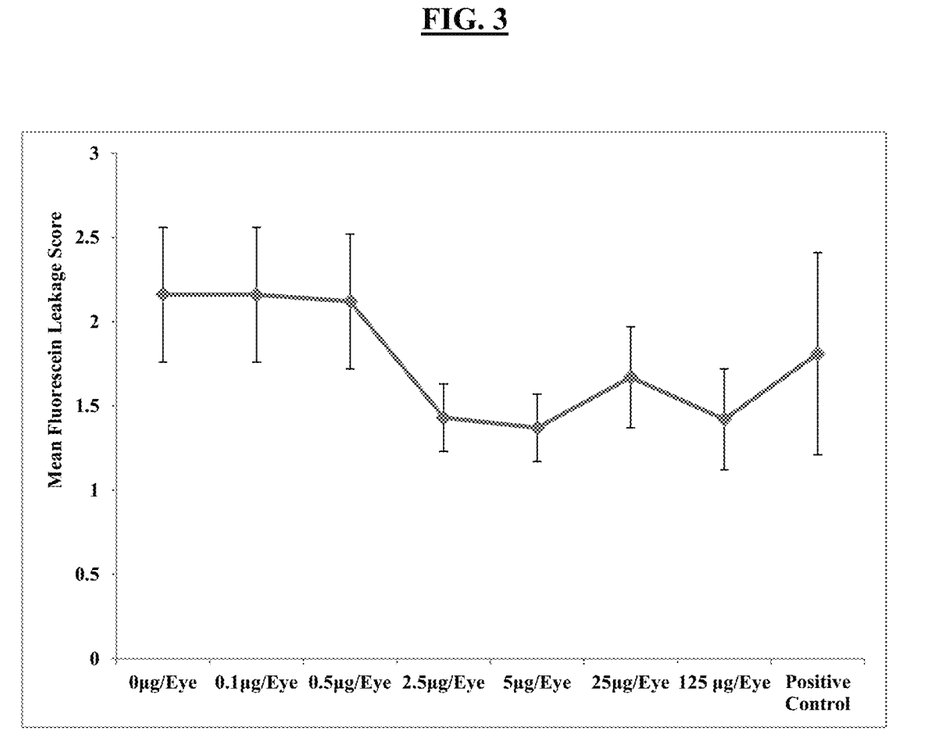
FIG. 3 depicts the relationship between the mean fluorescein leakage and the dosage.

One day before the administration, there was no significant difference in the mean fluorescein Leakage score between the control group (p>0.05) and other groups with treatment. The mean fluorescein leakage score is calculated as follows:

Mean fluorescein leakage score=[(number of grade 0 light spot×0)+(number of grade 1 light spot×1)+(number of grade 2 light spot×2)+(number of grade 3 light spot×3)]÷the sum of four kinds of light spots After treatment, the mean fluorescein leakage score in the positive control group and groups 3-6 significantly decreased compared to the model group (the group without any treatment). There was no statistically significant difference between groups 7 and 8. Without being bound by a theory, the results show that nintedanib ethanesulfonate can inhibit the leakage caused by CNV. Compared to the positive control group, the leakage significantly decreased in group 5 (p≤0.05). (FIG. 3).

Without being bound by a theory, the results show that administration of nintedanib ethanesulfonate eye drops at various dosages (125 µg/eye, 25 µg/eye, 5 µg/eye, 2.5 µg/eye, 0.5 µg/eye) can inhibit the ratios of light spots and mean fluorescein leakage score, and the development of CNV in the laser photocoagulation-induced rats.

Equivalents

It is to be understood that while the disclosure has been described in conjunction with the above embodiments, the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs.

The embodiments illustratively described herein may suitably be practiced in the absence of any element or elements, or limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement, and variation of the embodiments herein disclosed may be resorted to by those skilled in the art, and that such modifications, improvements, and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method of treating choroidal neovascularization (CNV), comprising administering an effective amount of a pharmaceutical composition to an eye of a human subject in need thereof, wherein the pharmaceutical composition comprises nintedanib ethanesulfonate, wherein the pharmaceutical composition is a formulation, comprising (1) 0.5 to 20 mg/mL nintedanib ethanesulfonate, (2) 50 to 200 mg/mL medium chain triglyceride, (3) 5 to 30 mg/mL soybean lecithin, (4) 2 to 20 mg/mL cholesterol, (5) 5 to 50 mg/mL glycerin, (6) 0.05 to 0.5 mg/mL benzalkonium chloride, and (7) 0.1 to 1 mg/mL vitamin E.

2. The method of claim 1, wherein the pharmaceutical composition comprises 0.5 mg/mL to 4 mg/mL nintedanib ethanesulfonate.

3. The method of claim 1, wherein the pharmaceutical composition further comprises an age-related macular degeneration (AMD) therapeutic agent comprising a vascular endothelial growth factor (VEGF) inhibitor, a platelet-derived growth factor (PDGF) inhibitor, or a fibroblast growth factor (FGF) inhibitor.

4. The method of claim 1, wherein the pharmaceutical composition further comprises an angiogenesis inhibitor.

5. The method of claim 1, wherein the pharmaceutical composition is in form of an eye drop, an oculentum, a collyrium, an ointment, a lysosome, a gel, a liquid, a liposome, a microcapsule, a microsphere, or an intraocular injection.

6. The method of claim 1, wherein the pharmaceutical composition is a formulation, comprising
  (1) 1 to 20 mg/mL nintedanib ethanesulfonate,
  (2) 50 to 200 mg/mL medium chain triglyceride,
  (3) 5 to 30 mg/mL soybean lecithin,
  (4) 2 to 20 mg/mL cholesterol,
  (5) 5 to 50 mg/mL glycerin,
  (6) 0.05 to 0.5 mg/mL benzalkonium chloride, and
  (7) 0.1 to 1 mg/mL vitamin E.

7. The method of claim 6, wherein the pharmaceutical formulation comprises 7 to 15 mg/mL nintedanib ethanesulfonate.

* * * * *